United States Patent
Handa et al.

(10) Patent No.: US 9,061,269 B2
(45) Date of Patent: Jun. 23, 2015

(54) METHOD FOR PRODUCING WATER-ABSORBENT RESIN

(75) Inventors: Masayoshi Handa, Himeji (JP); Koji Ueda, Himeji (JP); Kimihiko Kondo, Himeji (JP)

(73) Assignee: SUMITOMO SEIKA CHEMICALS CO., LTD., Kako-Gun (JP)

( * ) Notice: Subject to any disclaimer, the term of this patent is extended or adjusted under 35 U.S.C. 154(b) by 0 days.

(21) Appl. No.: 13/993,823

(22) PCT Filed: Jan. 23, 2012

(86) PCT No.: PCT/JP2012/051358
§ 371 (c)(1),
(2), (4) Date: Jun. 13, 2013

(87) PCT Pub. No.: WO2012/108253
PCT Pub. Date: Aug. 16, 2012

(65) Prior Publication Data
US 2013/0274088 A1    Oct. 17, 2013

(30) Foreign Application Priority Data
Feb. 8, 2011 (JP) ................. 2011-025014

(51) Int. Cl.
*B01J 20/30* (2006.01)
*B01J 20/26* (2006.01)
(Continued)

(52) U.S. Cl.
CPC ............ *B01J 20/3028* (2013.01); *C08F 2/32* (2013.01); *B01J 20/261* (2013.01); *A61L 15/60* (2013.01); *C08F 2/001* (2013.01)

(58) Field of Classification Search
CPC .......... C08F 120/20; C08F 2/32; B01J 20/30; B01J 20/26
USPC .......................................... 526/317.1; 502/7
See application file for complete search history.

(56) References Cited

U.S. PATENT DOCUMENTS

| 5,994,419 A | 11/1999 | Collette et al. |
| 2007/0179261 A1 | 8/2007 | Uda et al. |

(Continued)

FOREIGN PATENT DOCUMENTS

| CN | 101835809 A | 9/2010 |
| EP | 0522570 A1 | 1/1993 |

(Continued)

OTHER PUBLICATIONS

International Preliminary Report on Patentability and Written Opinion issued Aug. 13, 2013, in PCT International Application No. PCT/JP2012/051358.

(Continued)

*Primary Examiner* — Michael M Bernshteyn
(74) *Attorney, Agent, or Firm* — Birch, Stewart, Kolasch & Birch, LLP

(57) ABSTRACT

A method for producing a water-absorbent resin by a reversed-phase suspension polymerization method, includes step 1 of dispersing a first aqueous solution containing a partially neutralized product (A) of a water-soluble ethylenically unsaturated monomer having acid groups in the molecule in a petroleum-type hydrocarbon dispersion medium in the presence of a dispersing agent, and then polymerizing the resulting dispersion to obtain a slurry containing primary particles of a polymer, and step 2 of adding a second aqueous solution containing a partially neutralized product (B) of a water-soluble ethylenically unsaturated monomer having acid groups in the molecule to the slurry obtained in step 1, and then polymerizing the mixture to obtain a slurry in which the primary particles are agglomerated. In the method, a molar neutralization degree X of the partially neutralized product (A) and a molar neutralization degree Y of the partially neutralized product (B) are defined.

9 Claims, 1 Drawing Sheet

(51) Int. Cl.
  *C08F 120/20* (2006.01)
  *C08F 2/32* (2006.01)
  *A61L 15/60* (2006.01)
  *C08F 2/00* (2006.01)

(56) References Cited

U.S. PATENT DOCUMENTS

2010/0036004 A1  2/2010  Harren et al.
2010/0331802 A1  12/2010  Yokoyama et al.

FOREIGN PATENT DOCUMENTS

| JP | 61-87702 A | 5/1986 |
| JP | 62-28402 A | 2/1987 |
| JP | 62-172006 A | 7/1987 |
| JP | 9-143210 A | 6/1997 |
| JP | 10-147606 A | 6/1998 |
| JP | 10147606 A * | 6/1998 |
| JP | 2000-80109 A | 3/2000 |
| JP | 2001-11106 A | 1/2001 |
| JP | 2008-297422 A | 12/2008 |
| JP | 2010-94656 A | 4/2010 |
| JP | 2010094656 A * | 4/2010 |
| JP | 2010-518213 A | 5/2010 |
| WO | WO 2005/083825 A1 | 7/2005 |

OTHER PUBLICATIONS

International Search Report issued May 1, 2012, in PCT International Application No. PCT/JP2012/051358.
The Extended European Search Report for European Patent Appl. No. 12744982.5 dated Jul. 2, 2014.
Chinese Search Report, dated Sep. 4, 2014, for Chinese Application No. 201280008185.X.
Singapore Search Report and Written Opinion, dated Oct. 2, 2014, for Singapore Application No. 2013059936.

* cited by examiner

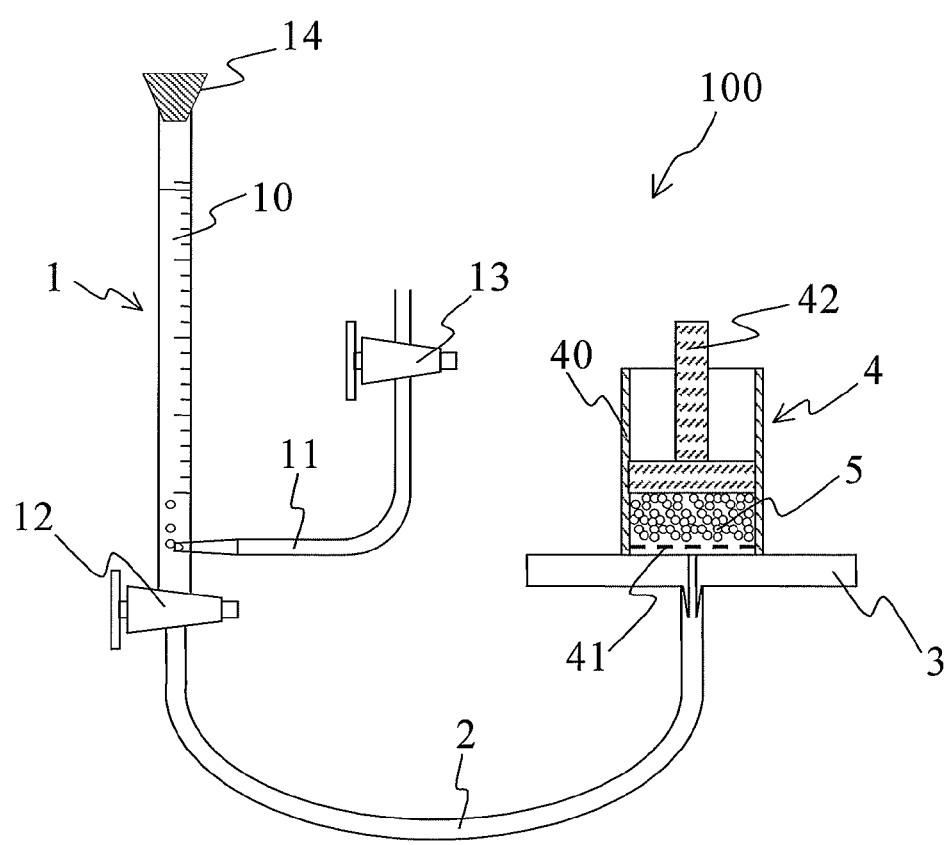

METHOD FOR PRODUCING WATER-ABSORBENT RESIN

TECHNICAL FIELD

The present invention relates to a method for producing a water-absorbent resin, and particularly to a method for producing a water-absorbent resin by a reversed-phase suspension polymerization method.

BACKGROUND ART

Sanitary supplies such as paper diapers and sanitary napkins, and absorbent articles such as so-called pet sheets for pet animals are generally produced using a lot of synthetic resins and modifying agents, such as top sheets, back sheets, hot-melt adhesives, stretchable materials, water-absorbent resins and pulp fibers, and therefore can sometimes generate odor originating from raw material components. Since sanitary supplies are applied to the human body, even slight odor may make users uncomfortable and it is required to make the sanitary supplies odorless. In particular, a water-absorbent resin as a main material of sanitary supplies has slight odor originating from a substance which is used in the production process and the odor is likely to be generated at the time of water absorption. Therefore, it is strongly desired to reduce odor of a water-absorbent resin per se.

There are known, as a water-absorbent resin to be used in sanitary supplies, a partially neutralized polyacrylic acid, a neutralized product of a starch-acrylic acid graft polymer, a hydrolyzate of a starch-acrylonitrile graft polymer, a saponified product of a vinyl acetate-acrylic acid ester copolymer and the like. It is considered that the cause of odor generated by the water-absorbent resin lies mainly in the production method. That is, since the water-absorbent resin to be used for sanitary supplies is generally in the form of a powder, it is often produced by a reversed-phase suspension polymerization method by which a powdered water-absorbent resin is easily produced. According to the polymerization method, an aqueous monomer solution is suspended in a dispersion medium and the obtained suspension is polymerized, and thus the dispersion medium can be one reason of odor from the water-absorbent resin.

There are known, as the method for producing a water-absorbent resin by a reversed-phase suspension polymerization method, various methods, for example, a method in which a sucrose fatty acid ester is used as a protective colloidal agent when an $\alpha,\beta$-unsaturated carboxylic acid and an aqueous solution of an alkali metal salt thereof are polymerized in a petroleum-type hydrocarbon solvent in the presence or absence of a crosslinking agent using a radical polymerization initiator (Patent Literature 1), a method in which a polyglyceryl fatty acid ester having an HLB of 2 to 16 is used as a surfactant when an $\alpha,\beta$-unsaturated carboxylic acid and an aqueous solution of 25% by mass or more of an alkali metal salt thereof are polymerized in a petroleum-type hydrocarbon solvent in the presence or absence of a crosslinking agent using a radical polymerization initiator (Patent Literature 2) and the like. However, all the production methods aim at improving water absorption capacity and do not pay attention to odor, and it cannot be said that any obtained water-absorbent resin suppresses odor.

Also, sanitary supplies have a problem of odor from another point of view. That is, since sanitary supplies aim at absorption of body fluids such as human urine and blood, there is a problem that suppression of odor, for example ammonia odor, generated with the lapse of time after absorption of a body fluid is required. It is also considered that odor is suppressed by using a sterilizer. However, in sanitary supplies to which harmlessness is particularly required, odor is generally suppressed by controlling the pH of a water-absorbent resin per se, or the pH of an absorbent material using a water-absorbent resin. For example, Patent Literature 3 describes a method in which a pH adjustor such as an organic acid like citric acid or adipic acid, a polyacrylic acid having a neutralization degree of 50% or less, or an ion-exchanging cellulose layer is added in an absorbent material. Also, Patent Literature 4 describes a method in which a water-absorbent polymer having a neutralization degree of 70 mol % or less is coated by being brought into contact with an acidic component of an aqueous organic acid solution such as an aqueous citric acid solution. Furthermore, Patent Literature 5 describes a method in which fine particles are fixed on a surface of an acid group-containing water-absorbent resin particle by treating the resin particle with an acid group-containing radical polymerizable compound thereby adjusting an acid group neutralization index at the surface of an absorbent to less than that in the interior thereof.

However, the method of Patent Literature 3 has a problem in economical efficiency since the pH adjustor is expensive. Moreover, since the pH adjustor per se has no liquid absorbency, absorption characteristics of an absorbent material may be impaired. The method of Patent Literature 4 has a problem in economical efficiency since an acidic component is expensive, and also the coating step is complicated. Furthermore, the method of Patent Literature 5 has low practicability since the production process is complicated and troublesome, and also the unreacted acid group-containing radical polymerizable compound may remain and therefore application of the obtained absorbent to sanitary supplies has safety concerns.

PRIOR ART LITERATURES

Patent Literatures

Patent Literature 1: Japanese Patent Application Laid-Open No. 61-087702
Patent Literature 2: Japanese Patent Application Laid-Open No. 62-172006
Patent Literature 3: Japanese Patent Application Laid-Open No. 62-028402
Patent Literature 4: Japanese Patent Application Laid-Open No. 2010-518213
Patent Literature 5: Japanese Patent Application Laid-Open No. 2010-094656

SUMMARY OF THE INVENTION

Problems to be Solved by the Invention

An object of the present invention is to suppress odor originating from a dispersion medium and odor generated with the lapse of time after absorption of a body fluid or the like by a simple method, with respect to a water-absorbent resin produced by a reversed-phase suspension polymerization method.

Means for Solving the Problems

The present inventors have found that, in case of producing a water-absorbent resin by a reversed-phase suspension polymerization method, when an aqueous solution containing a partially neutralized product of a water-soluble ethylenically unsaturated monomer having acid groups in the molecule is allowed to undergo multi-stage reversed-phase suspension polymerization in a petroleum-type hydrocarbon dispersion medium, and also a molar neutralization degree of a partially neutralized product contained in the aqueous solution used in each polymerization stage is controlled, the amount of the petroleum-type hydrocarbon dispersion medium remaining in the obtained water-absorbent resin remarkably decreases, and thus odor of the water-absorbent resin per se can be significantly suppressed. They have also found that, when the thus obtained water-absorbent resin absorbs a body fluid or the like, it is possible to suppress formation of an odor substance such as ammonia which can cause the generation of odor with the lapse of time.

The present invention has been completed based on these results. The present invention is directed to a method for producing a water-absorbent resin by a reversed-phase suspension polymerization method, the method including step 1 of dispersing a first aqueous solution containing a partially neutralized product (A) of a water-soluble ethylenically unsaturated monomer having acid groups in the molecule in a petroleum-type hydrocarbon dispersion medium in the presence of a dispersing agent, and then polymerizing the resulting dispersion to obtain a slurry containing primary particles of a polymer, and step of adding a second aqueous solution containing a partially neutralized product (B) of a water-soluble ethylenically unsaturated monomer having acid groups in the molecule to the slurry obtained in step 1, and then polymerizing the resulting mixture to obtain a slurry in which the primary particles are agglomerated, wherein a molar neutralization degree X of the partially neutralized product (A) is set larger than a molar neutralization degree Y of the partially neutralized product (B), and also a difference between the molar neutralization degree X and the molar neutralization degree Y is set to 5% or more. The dispersing agent to be used herein is at least one member selected from the group consisting of a surfactant and a polymer-type dispersing agent.

In this production method, the addition and polymerization of the second aqueous solution may be repeated in step 2.

In a preferred mode of this production method, the molar neutralization degree X is set to 65 to 94%, and also the molar neutralization degree Y is set to 56 to 89%.

The water-soluble ethylenically unsaturated monomer having acid groups in the molecule to be used in this production method is, for example, at least one member among those of acrylic acid and methacrylic acid. The surfactant is at least one kind selected from the group consisting of a polyglyceryl fatty acid ester, a sucrose fatty acid ester and a sorbitan fatty acid ester. Furthermore, the polymer-type dispersing agent is at least one kind selected from the group consisting of a maleic anhydride-modified polyethylene, a maleic anhydride-modified polypropylene, a maleic anhydride-modified ethylene-propylene copolymer, a maleic anhydride-ethylene copolymer, a maleic anhydride-propylene copolymer, a maleic anhydride-ethylene-propylene copolymer, a polyethylene, a polypropylene, an ethylene-propylene copolymer, an oxidized polyethylene, an oxidized polypropylene and an oxidized ethylene-propylene copolymer.

In this production method, it is preferred that the first aqueous solution is dispersed in the petroleum-type hydrocarbon solvent containing the polymer-type dispersing agent, and the surfactant is further added to the obtained dispersion, and then the resulting mixture is polymerized in step 1.

This production method further includes step 3 of post-crosslinking the water-absorbent resin obtained in step 2 using a post-crosslinking agent. In this case, the post-crosslinking agent to be used is usually at least one kind selected from the group consisting of ethylene glycol diglycidyl ether, polyethylene glycol diglycidyl ether, ethylene glycol triglycidyl ether, polyethylene glycol triglycidyl ether, glycerol diglycidyl ether, polyglycerol diglycidyl ether, glycerol triglycidyl ether, polyglycerol triglycidyl ether, propylene glycol polyglycidyl ether, polypropylene glycol polyglycidyl ether, glycerol polyglycidyl ether and polyglycerol polyglycidyl ether.

In the production method of the present invention, an aqueous solution containing a partially neutralized product of a water-soluble ethylenically unsaturated monomer having acid groups in the molecule is allowed to undergo multi-stage reversed-phase suspension polymerization in a petroleum-type hydrocarbon dispersion medium, and also a molar neutralization degree of a partially neutralized product contained in the aqueous solution used in each polymerization stage is controlled. Therefore, it is possible by the method to produce a water-absorbent resin of which odor originating from the petroleum-type hydrocarbon dispersion medium is suppressed, and also which can suppress formation of an odor substance such as ammonia after absorption of a body fluid or the like.

The present invention according to another standpoint is directed to an absorbent material, and this absorbent material includes the water-absorbent resin obtainable by the production method according to the present invention, and a hydrophilic fiber.

The present invention according to still another standpoint is directed to an absorbent article, and this absorbent article includes a liquid permeable sheet, a liquid impermeable sheet, and the absorbent material of the present invention retained in between these sheets.

The absorbent material and absorbent article of the present invention are produced by using a water-absorbent resin produced by the production method of the present invention. Therefore, odor of the absorbent material and absorbent article per se is significantly suppressed, and also formation of an odor substance derived from an absorbed body fluid or the like can be suppressed.

Other objects and results of the present invention will be mentioned in the following detailed description.

BRIEF DESCRIPTION OF THE DRAWINGS

FIG. 1 A schematic view of an apparatus used in Examples for the measurement of a water absorption capacity under a load.

EMBODIMENTS OF THE INVENTION

In the method for producing a water-absorbent resin according to the present invention, an aqueous solution containing a partially neutralized product of a water-soluble ethylenically unsaturated monomer having acid groups in the molecule is applied to a multi-stage reversed-phase suspension polymerization method.

The partially neutralized product of a water-soluble ethylenically unsaturated monomer having acid groups in the molecule to be used herein is a product obtained by partially neutralizing acid groups of a water-soluble ethylenically unsaturated monomer having acid groups in the molecule. Examples of the water-soluble ethylenically unsaturated monomer having acid groups in the molecule include those having carboxyl groups as acid groups, such as acrylic acid, methacrylic acid, 2-acrylamide-2-methylpropanesulfonic acid, 2-methacrylamide-2-methylpropanesulfonic acid and maleic acid. These monomers may be used alone, or two or more kinds of them may be used in combination.

It is particularly preferable to use, as the water-soluble ethylenically unsaturated monomer having acid groups in the molecule, acrylic acid or methacrylic acid or a mixture thereof since it is easily available industrially and also the water-absorbent resin to be obtained has satisfactory water absorption performance.

The partially neutralized product of a water-soluble ethylenically unsaturated monomer having acid groups in the molecule is a product obtained by partially neutralizing the acid groups with an alkali compound to form a salt. Examples of the alkali compound to be used for neutralization usually include various compounds of lithium, sodium, potassium or ammonium, for example, hydroxides, carbonates and hydrogen carbonates. It is particularly preferable to use a compound of sodium or potassium since it is easily available industrially or it is easy to prepare, and also the water-absorbent resin to be obtained has satisfactory water absorption performance.

In the production method of the present invention, at least two kinds, each having a different molar neutralization degree, are used as a partially neutralized product of a water-soluble ethylenically unsaturated monomer having acid groups in the molecule (hereinafter sometimes simply referred a "partially neutralized product") according to the stage of a multi-stage reversed-phase suspension polymerization method. That is, in the present invention, at least two kinds, for example, a partially neutralized product (A) to be used in a first polymerization stage of a reversed-phase suspension polymerization method, and a partially neutralized product (B), having a molar neutralization degree different from that of the partially neutralized product (A), to be used in the second stage or subsequent stages of the polymerization method are prepared.

Herein, the molar neutralization degree X of the partially neutralized product (A) is set to the value larger than the molar neutralization degree Y of the partially neutralized product (B). A difference (X−Y) between the molar neutralization degree X of the partially neutralized product (A) and the molar neutralization degree Y of the partially neutralized product (B) is set to 5% or more. It is possible to produce the objective water-absorbent resin, which exerts the below-mentioned odor suppression result, by properly choosing partially neutralized products, which differ in the molar neutralization degree, in the multi-stage reversed-phase suspension polymerization method. From the viewpoint of enhancing the below-mentioned odor suppression result, a difference between the molar neutralization degree X and the molar neutralization degree Y is preferably set to 10% or more, more preferably 15% or more, and particularly preferably 20% or more.

The molar neutralization degree X of the partially neutralized product (A) is usually set to 65 to 94%, preferably 70 to 90%, more preferably 75 to 85%, and particularly preferably 80 to 85%. On the other hand, the molar neutralization degree Y of the partially neutralized product (B) is usually set to 56 to 89%, more preferably 60 to 85%, still more preferably 65 to 80%, yet still more preferably 65 to 75%, and particularly preferably 65 to 70%.

With respect to a combination of the molar neutralization degree X of the partially neutralized product (A) and the molar neutralization degree Y of the partially neutralized product (B), in addition to the above-mentioned conditions, in the water-absorbent resin obtained by a multi-stage reversed-phase suspension polymerization method, a molar neutralization degree Z of acid groups originating from the partially neutralized product (A) and the partially neutralized product (B) is preferably selected from 60 to 90%, more preferably 65 to 85%, and still more preferably 70 to 80%. The obtained water-absorbent resin can easily achieve the below-mentioned odor suppression result by selecting the molar neutralization degree Z as described above. When the molar neutralization degree Z is less than 60%, acid groups are less likely to be ionized, and thus water absorption capacity of the water-absorbent resin may decrease. In contrast, when the neutralization degree Z exceeds 90%, the water-absorbent resin may cause skin irritation in case of using it for sanitary supplies.

In the present invention, each molar neutralization degree is the value determined by calculating from the kind and usage of raw materials used at the time of preparation of a partially neutralized product.

The aqueous solution containing a partially neutralized product (A) or a partially neutralized product (B) (hereinafter sometimes referred to as an "aqueous monomer solution") may contain other monomers which are copolymerizable with the partially neutralized product (A) or partially neutralized product (B). Examples of the monomer (hereinafter sometimes referred to as a "monomer (C)") include nonionic unsaturated monomers such as acrylamide, methacrylamide, N,N-dimethylacrylamide, N,N-dimethylmethacrylamide, 2-hydroxyethyl acrylate, 2-hydroxyethyl methacrylate, N-methylolacrylamide and N-methylolmethacrylamide; amino group-containing unsaturated monomers such as diethylaminoethyl acrylate, diethylaminoethyl methacrylate, diethylaminopropyl acrylate and diethylaminopropyl methacrylate; and quaternized products thereof.

In the aqueous monomer solution, a molar ratio of the monomer (C) to the partially neutralized product (A) or partially neutralized product (B) (partially neutralized product (A) or partially neutralized product (B): monomer (C)) is preferably set within a range from 100:0 to 60:40, more preferably from 100:0 to 70:30, and still more preferably from 100:0 to 80:20.

In the aqueous monomer solution, total concentration of the partially neutralized product (A) or partially neutralized product B and the monomer (C) is usually set within a range of 20% by mass or more and a saturated concentration or less, preferably from 30 to 55% by mass, and more preferably from 35 to 46% by mass. The aqueous monomer solution can maintain high productivity of the water-absorbent resin while avoiding a rapid reaction by setting the total concentration within the above range.

The aqueous monomer solution may optionally contain an internal crosslinking agent. Examples of the internal crosslinking agent include polyols such as ethylene glycol, polyethylene glycol, 1,4-butanediol, glycerin and trimethylolpropane; polyunsaturated esters having two or more vinyl groups obtained by reacting polyols with unsaturated acids such as acrylic acid and methacrylic acid; bisacrylamides such as N,N'-methylenebisacrylamide; and polyglycidyl compounds having two or more glycidyl groups, such as ethylene glycol diglycidyl ether, polyethylene glycol diglycidyl ether, ethylene glycol triglycidyl ether, polyethylene glycol triglycidyl ether, glycerol diglycidyl ether, polyglycerol diglycidyl ether, glycerol triglycidyl ether, polyglycerol triglycidyl ether, propylene glycol polyglycidyl ether, polypropylene glycol polyglycidyl ether, glycerol polyglycidyl ether and polyglycerol polyglycidyl ether. These internal crosslinking agents may be used alone, or two or more kinds of them may be used in combination.

The usage of the internal crosslinking agent is preferably 3 parts by mass or less, more preferably 1 part by mass or less, and still more preferably from 0.001 to 0.1 part by mass, relative to 100 parts by mass of the total amount of the partially neutralized product (A) or (B) and the monomer (C) contained in the aqueous monomer solution. When the usage exceeds 3 parts by mass, water absorption performance of the water-absorbent resin to be obtained may be impaired because of excess crosslinking.

The aqueous monomer solution may further contain a chain-transfer agent and a thickener, optionally. Examples of usable chain-transfer agents include compounds such as thiols, thiolic acids, secondary alcohols, hypophosphorous acid and phosphorous acid. These chain-transfer agents may be used alone, or two or more kinds of them may be used in combination. Examples of usable thickeners include carboxymethyl cellulose, hydroxyethyl cellulose, hydroxypropyl cellulose, methyl cellulose, polyethylene glycol, polyacrylic acid, neutralized polyacrylic acid, and polyacrylamide. These thickeners may be used alone, or two or more kinds of them may be used in combination.

In the polymerization of an aqueous monomer solution by a multi-stage reversed-phase suspension polymerization method, first, an aqueous monomer solution containing a partially neutralized product (A) (hereinafter sometimes referred to as a "first aqueous solution") is added and dispersed in a petroleum-type hydrocarbon dispersion medium in the presence of a dispersing agent, and then first-stage polymerization is carried out (step 1). The dispersing agent to be used herein is at least one member among those of a surfactant and a polymer-type dispersing agent. In this step, dispersion of the first aqueous solution in the petroleum-type hydrocarbon dispersion medium is preferably carried out by adding and dispersing the first aqueous solution in the petroleum-type hydrocarbon dispersion medium containing a polymer-type dispersing agent added therein in advance, and then a surfactant is further added and dispersed in the dispersion thereof. According to such preferable first-stage polymerization, the amount of the petroleum-type hydrocarbon dispersion medium remaining in the obtained water-absorbent resin is effectively reduced, and thus odor of the water-absorbent resin per se can be effectively suppressed.

Examples of petroleum-type hydrocarbon dispersion medium usable herein include aliphatic hydrocarbons having 6 to 8 carbon atoms such as n-hexane, n-heptane, 2-methylhexane, 3-methylhexane and n-octane; alicyclic hydrocarbons having 6 to 8 carbon atoms such as cyclohexane, methylcyclopentane and methylcyclohexane; aromatic hydrocarbons such as benzene, toluene and xylene; and any mixtures thereof. At least one kind selected from among aliphatic hydrocarbons having 6 to 7 carbon atoms and alicyclic hydrocarbons having 6 to 7 carbon atoms is preferably used since they are easily available industrially and are inexpensive.

The usage of the petroleum-type hydrocarbon dispersion medium is preferably set within a range from 40 to 600 parts by mass, more preferably from 50 to 400 parts by mass, and still more preferably from 60 to 200 parts by mass, relative to 100 parts by mass of the first aqueous solution since the first aqueous solution can be uniformly dispersed and also the polymerization temperature is easily controlled.

Examples of surfactants usable herein include nonionic surfactants such as sorbitan fatty acid esters, polyoxyethylene sorbitan fatty acid esters, polyglyceryl fatty acid esters, polyoxyethylene glyceryl fatty acid esters, sucrose fatty acid esters, sorbitol fatty acid esters, polyoxyethylene sorbitol fatty acid esters, polyoxyethylene alkyl ether, polyoxyethylene alkyl phenyl ether, polyoxyethylene castor oil, polyoxyethylene hydrogenated castor oil, alkylallylformaldehyde condensed polyoxyethylene ether, polyoxyethylene polyoxypropyl alkyl ether, polyethylene glycol fatty acid ester, alkyl glucoside, N-alkylgluconamide, polyoxyethylene fatty acid amide and polyoxyethylene alkyl amine; and anionic surfactants such as fatty acid salt, alkylbenzenesulfonic acid salt, alkyl methyl tauric acid salt, polyoxyethylene alkylphenyl ether sulfuric acid ester salt, polyoxyethylene alkyl ether sulfuric acid ester salt, polyoxyethylene alkyl ether sulfonic acid and a salt thereof, polyoxyethylene alkyl phenyl ether phosphoric acid and a salt thereof and polyoxyethylene alkyl ether phosphoric acid and a salt thereof. These surfactants may be used alone, or two or more kinds of them may be used in combination. Among these surfactants, a nonionic surfactant, in particular, at least one kind among those of polyglyceryl fatty acid esters, sucrose fatty acid esters and sorbitan fatty acid esters is preferably used from the viewpoint of dispersion stability of the first aqueous solution in the petroleum-type hydrocarbon dispersion medium.

There is no particular limitation on the HLB value of the surfactant, since the form of primary particles of a polymer obtained by the first-stage polymerization varies depending on the kind of the surfactant to be used. For example, a surfactant having the HLB value within a range of 5 or less is preferably used in case of a sucrose fatty acid ester or a sorbitan fatty acid ester, while a surfactant having the HLB value within a range of 10 or less is preferably used in case of a polyglyceryl fatty acid ester.

The usage of the surfactant is preferably from 0.01 to 5 parts by mass, and more preferably from 0.05 to 3 parts by mass, relative to 100 parts by mass of the first aqueous solution. When the usage of the surfactant is less than 0.01 part by mass, dispersion stability of the first aqueous solution in the petroleum-type hydrocarbon dispersion medium may deteriorate. In contrast, when the usage exceeds 5 parts by mass, the result corresponding to the usage is less likely to be obtained, and thus economical efficiency may be impaired.

There is no particular limitation on the method of adding a surfactant to the petroleum-type hydrocarbon dispersion medium, and it is possible to use a method in which a surfactant is added to a first aqueous solution in advance, and a method in which a surfactant is directly added to a petroleum-type hydrocarbon dispersion medium. In the latter case, since the first aqueous solution can be dispersed and stabilized within a short time, the surfactant is preferably diluted with or dissolved in a small amount of the petroleum-type hydrocarbon dispersion medium in advance for use.

Examples of polymer-type dispersing agents usable herein include a maleic anhydride-modified polyethylene, a maleic anhydride-modified polypropylene, a maleic anhydride-modified ethylene-propylene copolymer, a maleic anhydride-ethylene copolymer, a maleic anhydride-propylene copolymer, a maleic anhydride-ethylene-propylene copolymer, a polyethylene, a polypropylene, an ethylene-propylene copolymer, an oxidized polyethylene, an oxidized polypropylene, an oxidized ethylene-propylene copolymer, an ethylene-acrylic acid copolymer, ethyl cellulose, ethylhydroxyethyl cellulose, a maleic anhydride-modified polybutadiene, a maleic anhydride-modified EPDM (ethylene/propylene/diene terpolymer) and the like. These polymer-type dispersing agents may be used alone, or two or more kinds of them may be used in combination.

Among the polymer-type dispersing agents, it is particularly preferred to use at least one kind among those of a maleic anhydride-modified polyethylene, a maleic anhydride-modified polypropylene, a maleic anhydride-modified ethylene-propylene copolymer, a maleic anhydride-ethylene copolymer, a maleic anhydride-propylene copolymer, a maleic anhydride-ethylene-propylene copolymer, a polyethylene, a polypropylene, an ethylene-propylene copolymer, an oxidized polyethylene, an oxidized polypropylene and an oxidized ethylene-propylene copolymer.

Since the polymer-type dispersing agent is preferably dissolved or dispersed in the petroleum-type hydrocarbon dispersion medium before use, a polymer-type dispersing agent having a mass average molecular weight of 20,000 or less is preferably used. In particular, it is preferred to use a polymer-type dispersing agent having a mass average molecular weight of 10,000 or less, and more preferably 5,000 or less.

The usage of the polymer-type dispersing agent is preferably set to 5 parts by mass or less, relative to 100 parts by mass of the first aqueous solution. In particular, the usage is preferably set within a range from 0.01 to 3 parts by mass, and more preferably from 0.05 to 2 parts by mass. When the usage of the polymer-type dispersing agent exceeds 5 parts by mass, the result corresponding to the usage is less likely to be obtained, and thus economical efficiency may be impaired.

The first aqueous solution is polymerized while being dispersed in the petroleum-based hydrocarbon dispersion medium by stirring. Examples of the stirring blade used in the stirring include a propeller blade, a paddle blade, an anchor blade, a turbine blade, a pfaudler blade, a ribbon blade, Full Zone Blade (trade name of Shinko Pantec Co., Ltd.), Max Blend Blade (trade name of Sumitomo Heavy Industries, Ltd.), and Supermix (trade name of Satake Chemical Equipment Mfg., Ltd.).

The stirring conditions can be appropriately set according to the desired diameter of dispersion droplet of the first aqueous solution in the petroleum-type hydrocarbon dispersion medium. That is, the kind, blade diameter and rotational speed of the stirring blade can be appropriately selected so as to obtain the desired diameter of dispersion droplet of the first aqueous solution.

In the polymerization of the first aqueous solution, a water-soluble radical polymerization initiator is used. Examples of the water-soluble radical polymerization initiator include persulfates such as potassium persulfate, ammonium persulfate and sodium persulfate; peroxides such as hydrogen peroxide; and azo compounds such as 2,2'-azobis(2-amidinopropane)dihydrochloride, 2,2'-azobis[N-(2-carboxyethyl)-2-methylpropiondiamine]tetrahydrate, 2,2'-azobis(1-imino-1-pyrrolidino-2-methylpropane)dihydrochloride and 2,2'-azobis[2-methyl-N-(2-hydroxyethyl)-propionamide].

Among these polymerization initiators, potassium persulfate, ammonium persulfate, sodium persulfate and 2,2'-azobis(2-amidinopropane)dihydrochloride are preferred since they are easily available and easily handled. The water-soluble radical polymerization initiator may also be used in combination with a reducing agent such as a sulfite or ascorbic acid, in order to use it as a redox polymerization initiator.

Usually, the usage of the water-soluble radical polymerization initiator is preferably set within a range from 0.01 to 1 part by mass relative to 100 parts by mass of the total amount of monomers (i.e., the total amount of a partially neutralized product (A) and a monomer (C)) contained in the first aqueous solution. When the usage is less than 0.01 part by mass, the polymerization rate may decrease. In contrast, when the usage exceeds 1 part by mass, a rapid polymerization reaction occurs, and thus there is a problem with securing of safety.

There is no particular limitation on the timing of the addition of a water-soluble radical polymerization initiator to the reaction system. Usually, the water-soluble radical polymerization initiator is preferably added to the first aqueous solution in advance.

The reaction temperature at the time of polymerization of the first aqueous solution can be set according to the kind and amount of the polymerization initiator to be used, and thus cannot be completely determined. The reaction temperature is preferably set within a range from 20 to 100° C., and more preferably from 40 to 90° C. When the reaction temperature is lower than 20° C., the polymerization rate may decrease. In contrast, when the reaction temperature exceeds 100° C., a rapid polymerization reaction occurs, and thus there is a problem with securing of safety.

In case of using an internal crosslinking agent in the polymerization in step 1, it is preferred that the internal crosslinking agent is added to the first aqueous solution in advance, as described above. Alternatively, the internal crosslinking agent can be added to the petroleum-type hydrocarbon dispersion medium, in addition to the first aqueous solution.

A slurry containing primary particles of a polymer formed by polymerization of the partially neutralized product (A) and the monomer (C) contained in the first aqueous solution is obtained by step 1, that is, the first-stage polymerization step. Herein, the particle size (median particle size) of the primary particles is preferably set within a range from 20 to 200 μm, more preferably from 30 to 150 μm, and particularly preferably from 40 to 100 μm, so as to obtain a water-absorbent resin having a moderate agglomerated particle size by the below-mentioned step 2. This particle size is the value measured with respect to particles obtained by collecting a part of slurry which is obtained by the reaction after completion of the polymerization in step 1, followed by dewatering and drying. The particle size of the primary particles can be controlled by selecting the stirring conditions of the petroleum-type hydrocarbon dispersion medium and the reaction temperature.

Next, an aqueous monomer solution containing a partially neutralized product (B) (hereinafter sometimes referred to as a "second aqueous solution") is added to the slurry obtained in step 1 and the second-stage reversed-phase suspension polymerization is carried out to obtain a slurry of a water-absorbent resin having a desired particle size in which the primary particles obtained in step 1 are agglomerated (step 2).

Herein, it is usually necessary that an effect of the dispersing agent used in step 1 is reduced so that the second aqueous solution does not form independent droplets. Therefore, the dispersing agent is preferably precipitated by cooling the slurry obtained in step 1 before carrying out step 2.

In step 2, the slurry containing the second aqueous solution added therein is stirred and the reaction is carried out in the presence of the same water-soluble radical polymerization initiator as that used in step 1 while uniformly mixing the entire reaction system. The usage of the water-soluble radical polymerization initiator to be used herein is preferably set within a range from 0.01 to 1 part by mass relative to 100 parts by mass of the total amount of monomers (i.e., the total amount of a partially neutralized product (B) and a monomer (C)) contained in the second aqueous solution. When the usage is less than 0.01 part by mass, the primary particles are less likely to be agglomerated. In contrast, when the usage exceeds 1 part by mass, a rapid polymerization reaction occurs and thus there is a problem with securing of safety. There is no particular limitation on the timing of the addition of a water-soluble radical polymerization initiator to the reaction system. Usually, the water-soluble radical polymerization initiator is preferably added to the second aqueous solution in advance.

The reaction temperature in this step can be set according to the kind and amount of the water-soluble radical polymerization initiator to be used, and thus cannot be completely determined. Usually, the reaction temperature is preferably set within a range from 20 to 100° C., and more preferably from 40 to 90° C. When the reaction temperature is lower than 20° C., the primary particles are less likely to be agglomerated. In contrast, when the reaction temperature exceeds 100° C., a rapid polymerization reaction occurs and thus there is a problem with securing of safety.

In this step, the primary particles are agglomerated by polymerization of the monomer contained in the second aqueous solution to obtain a slurry containing agglomerated particles having a larger particle size. The median particle size of the agglomerated particles can be controlled by a state of precipitation of a dispersing agent from the slurry obtained in step 1, and the total amount of the monomers contained in the second aqueous solution to the total amount of the monomers contained in the first aqueous solution used in step 1. From this point of view, the amount of the second aqueous solution (in terms of the total amount of a partially neutralized product (B) and a monomer (C)) to be added in the present step is preferably from 50 to 300 parts by mass, more preferably from 80 to 220 parts by mass, still more preferably from 100 to 200 parts by mass, and particularly preferably from 120 to 180 parts by mass, relative to 100 parts by mass of the amount of first aqueous solution (in terms of the total amount of a partially neutralized product (A) and a monomer (C)) to be used in step 1 so as to obtain agglomerated particles having a moderate median particle size.

In step 2, for the purpose of adjusting the median particle size of agglomerated particles and improving productivity, the second aqueous solution is further added to the obtained slurry and the polymerization can be repeated. It is also possible to repeat such a manner of polymerization several times. The molar neutralization degree Y of the partially neutralized product (B) contained in the second aqueous solution to be used in this case is preferably the same as or less than the molar neutralization degree Y of the partially neutralized product (B) contained in the second aqueous solution used in the second-stage polymerization so that the deodorant result of the below-mentioned water-absorbent resin per se is not impaired.

In the production method of the present invention, the objective water-absorbent resin is obtained as a powdery form by applying a drying step of removing the petroleum-type hydrocarbon dispersion medium and moisture to the slurry obtained in step 2. The drying step can be carried out under normal pressure or under reduced pressure, and also can be carried out under a gas flow such as a nitrogen gas flow so as to improve drying efficiency. When the drying step is carried out under normal pressure, the drying temperature is preferably from 70 to 250° C., more preferably from 80 to 180° C., still more preferably from 80 to 140° C., and particularly preferably from 90 to 130° C. When the drying step is carried out under reduced pressure, the drying temperature is preferably from 60 to 100° C., and more preferably from 70 to 90° C.

The agglomerated particles obtained in step 2, that is, water-absorbent resin particles may be optionally subjected to a post-crosslinking treatment using a crosslinking agent. Since crosslinking density of a surface layer of the water-absorbent resin particles is increased by the post-crosslinking treatment, various characteristics such as water-absorption capacity under load, water-absorption rate and gel strength can be enhanced, and thus suitability as a water-absorbent resin for sanitary supplies can be enhanced.

The crosslinking agent to be used for a post-crosslinking treatment (hereinafter sometimes referred to as a "post-crosslinking agent") is preferably a crosslinking agent which has two or more functional groups having reactivity with a functional group originating from a partially neutralized product (A) or (B), and examples thereof include polyols such as ethylene glycol, propylene glycol, 1,4-butanediol, trimethylolpropane, glycerin, polyoxyethylene glycol, polyoxypropylene glycol and polyglycerin; polyglycidyl compounds such as ethylene glycol diglycidyl ether, polyethylene glycol diglycidyl ether, ethylene glycol triglycidyl ether, polyethylene glycol triglycidyl ether, glycerol diglycidyl ether, polyglycerol diglycidyl ether, glycerol triglycidyl ether, polyglycerol triglycidyl ether, propylene glycol polyglycidyl ether, polypropylene glycol polyglycidyl ether, glycerol polyglycidyl ether and polyglycerol polyglycidyl ether; haloepoxy compounds such as epichlorohydrin, epibromohydrin and α-methylepichlorohydrin; isocyanate compounds such as 2,4-tolylene diisocyanate and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol and 3-butyl-3-oxetane ethanol; oxazoline compounds such as 1,2-ethylenebisoxazoline; and carbonate compounds such as ethylene carbonate. These post-crosslinking agents may be used alone, or two or more kinds of them may be used in combination.

It is particularly preferred to select, as the post-crosslinking agent, a post-crosslinking agent, which per se is less likely to serve as a source of odor, so as to more effectively suppress the generation of odor from the water-absorbent resin. From such a point of view, among the above-mentioned post-crosslinking agents, it is particularly preferred to use at least one kind among those of ethylene glycol diglycidyl ether, polyethylene glycol diglycidyl ether, ethylene glycol triglycidyl ether, polyethylene glycol triglycidyl ether, glycerol diglycidyl ether, polyglycerol diglycidyl ether, glycerol triglycidyl ether, polyglycerol triglycidyl ether, propylene glycol polyglycidyl ether, polypropylene glycol polyglycidyl ether, glycerol polyglycidyl ether and polyglycerol polyglycidyl ether, each having excellent reactivity.

The usage of the post-crosslinking agent is usually set within a range from 0.005 to 5 parts by mass relative to 100 parts by mass of the total amount of the partially neutralized product (A) and the monomer (C) contained in the first aqueous solution, and the partially neutralized product (B) and the monomer (C) contained in the second aqueous solution. This usage is more preferably from 0.01 to 3 parts by mass, still more preferably from 0.02 to 1 part by mass, yet more preferably from 0.03 to 0.5 part by mass, and particularly preferably from 0.04 to 0.2 part by mass. When the addition amount of the post-crosslinking agent is less than 0.005 part by mass, various characteristics such as water-absorption capacity under load, water-absorption rate and gel strength of the obtained water-absorbent resin are less likely to be enhanced. In contrast, when the addition amount exceeds 5 parts by mass, not only water-absorption capacity of the obtained water-absorbent resin is rather impaired, but also the unreacted post-crosslinking agent may remain, and the obtained water-absorbent resin may generate odor from the unreacted post-crosslinking agent.

The post-crosslinking treatment can be carried out at any time after completion of step 2, and there is no particular limitation on the timing of execution. The post-crosslinking treatment is preferably carried out in the way of the drying step of the slurry obtained in step 2 under the residual amount of moisture within a range from 1 to 200 parts by mass, more preferably from 5 to 100 parts by mass, and still more preferably from 10 to 50 parts by mass, relative to 100 parts by mass of the obtained water-absorbent resin. The objective various characteristics can be enhanced more effectively by carrying out the post-crosslinking treatment in the presence of moisture thus controlled.

When the post-crosslinking treatment is applied, water and a hydrophilic organic solvent can be optionally used as a solvent. Examples of usable hydrophilic organic solvents include lower alcohols such as methyl alcohol, ethyl alcohol, n-propyl alcohol and isopropyl alcohol; ketones such as acetone and methyl ethyl ketone; ethers such as diethyl ether, dioxane and tetrahydrofuran; amides such as N,N-dimethylformamide; and sulfoxides such as dimethyl sulfoxide. These hydrophilic organic solvents may be used alone, or two or more kinds may be used in combination.

In order to enhance the result of suppressing odor generated from the water-absorbent resin per se, the solvent to be used herein is preferably a solvent with less odor, especially water, methyl alcohol or ethyl alcohol, and particularly preferably water.

The reaction temperature at the time of the post-crosslinking treatment is preferably from 50 to 250° C., more preferably from 60 to 180° C., still more preferably from 60 to 140° C., and particularly preferably from 70 to 120° C.

From the viewpoint of imparting moderate flowability, the water-absorbent resin obtained by the production method of the present invention is preferably dried so that the moisture content becomes 20% or less, and particularly 1 to 15% or 3 to 10%. In order to improve fluidity, the obtained water-absorbent resin can be used in the form of a mixture with an amorphous silica powder.

In the water-absorbent resin obtained by the production method of the present invention, the remaining amount of the petroleum-type hydrocarbon dispersion medium is usually controlled to 2,000 ppm or less, and particularly a trace amount of 1,500 ppm or less, 1,000 ppm or less, 500 ppm or less, 300 ppm or less, or 100 ppm or less depending on the production conditions. Therefore, odor of the water-absorbent resin per se can be suppressed very effectively. In particular, in case of using the water-absorbent resin in sanitary supplies, odor of the water-absorbent resin per se, which is likely to increase when a body fluid such as urine is absorbed, can be effectively suppressed. Therefore, the water-absorbent resin is less likely to make the human body uncomfortable. Although depending on the kind of the petroleum-type hydrocarbon dispersion medium, generally, when the remaining amount of the petroleum-type hydrocarbon dispersion medium is 2,000 ppm or less, olfactory sense of human being enables us to sense that odor is significantly suppressed in comparison with a water-absorbent resin obtained by a conventional production method in which attention is not paid to odor. When the remaining amount is 1,000 ppm or less, odor is less likely to be sensed, although it may vary between individuals. When the remaining amount is 100 ppm or less, it can be said that no odor is sensed without individual variation.

The water-absorbent resin obtained by the production method of the present invention is less likely to make the human body uncomfortable, and is therefore suited for application in sanitary supplies such as paper diapers and menstrual sanitary products. In case of using the water-absorbent resin in sanitary supplies, even after absorption of a body fluid such as urine or blood, it is possible to effectively suppress odor generated with the lapse of time, such as ammonia odor.

When the water-absorbent resin obtained by the present invention is intended for use in sanitary supplies, it is preferred to control the median particle size within a range from 200 to 800 µm by adjusting various conditions during production. The median particle size is more preferably from 250 to 600 µm, still more preferably from 300 to 550 µm, and particularly preferably from 350 to 500 µm.

When the water-absorbent resin obtained by the present invention is intended for use in sanitary supplies in the form of the below-mentioned absorbent material, there is a problem that the absorbent material partially becomes hard after compression if a lot of large particles are present in the water-absorbent resin. There is also a problem that, when a lot of small particles are present in the water-absorbent resin, the particles are likely to move in the absorbent material, and therefore uniformity of the absorbed material is impaired. Accordingly, the water-absorbent resin to be used in the absorbent material for sanitary supplies is preferably a water-absorbent resin having narrow particle size distribution, that is, a water-absorbent resin having less uniformity of particle size distribution. For this reason, in the production method of the present invention, it is preferred to control uniformity of particle size distribution of the water-absorbent resin within a range from 1.0 to 2.2, and particularly from 1.0 to 2.0 or 1.2 to 1.8, by adjusting various conditions during production.

The water-absorption capacity of the water-absorbent resin obtained by the present invention is usually 30 g/g or more at which gel blocking can be prevented and absorption capacity can be increased. In particular, the water-absorption capacity can be controlled more preferably within a range from 35 to 85 g/g, still more preferably from 40 to 75 g/g, and particularly preferably from 45 to 70 g/g, by adjusting various conditions during production.

The absorption capacity of saline solution under a load of the water-absorbent resin obtained by the present invention is usually 12 mL/g or more at which absorption characteristics of liquid are less likely to be impaired even when the water-absorbent resin is used under a load (under a load of 4.14 kPa). In particular, absorption capacity of saline solution under the same load can be more preferably controlled to 14 mL/g or more, still more preferably 16 mL/g or more, and particularly preferably 18 mL/g or more, by adjusting various conditions during production.

Furthermore, the pH of a gel of the water-absorbent resin obtained by the present invention usually becomes 3.5 to 7.5 at which less irritation to the skin arise and odor typified by ammonia generated after absorption of a body fluid can be more effectively suppressed. In particular, the pH of a gel can be preferably controlled within a range from 4.0 to 7.0, still more preferably from 4.5 to 6.5, and particularly preferably from 5.0 to 6.0, by adjusting various conditions during production.

The absorbent material of the present invention contains a water-absorbent resin obtainable by the production method of the present invention and hydrophilic fiber, and is used in sanitary supplies, for example, paper diapers and menstrual sanitary products. In the absorbent material, the water-absorbent resin and hydrophilic fiber are used, for example, in a uniformly blended mixing structure, a sandwich structure in which a water-absorbent resin is retained between layered hydrophilic fibers, or a packaging structure in which a mixture of a water-absorbent resin and a hydrophilic fiber is wrapped in a packaging sheet having liquid permeability, such as tissue paper.

It is possible to use, as the hydrophilic fiber, for example, cellulose fibers such as a cotton-like pulp obtained from wood, a mechanical pulp, a chemical pulp and a semi-chemical pulp; and artificial cellulose fibers such as rayon and acetate fibers. The hydrophilic fiber may contain, as a reinforcer of an absorbent material, fibers made of a synthetic resin such as polyamide, polyester or polyolefin.

The content of the water-absorbent resin in the absorbent material is usually from 10 to 90% by mass, preferably from 15 to 80% by mass, more preferably from 20 to 70% by mass, and still more preferably from 30 to 65% by mass. When the content of the water-absorbent resin is less than 10% by mass, the absorption capacity decreases, and thus liquid leakage and flow back may increase. In contrast, when the content exceeds 90% by mass, not only the cost of the absorbent material may increase, but also touch of the absorbent material may become hard. Therefore, there is inconvenience in use of the absorbent material in sanitary supplies.

The absorbent article of the present invention is an article in which an absorbent material of the present invention is retained between a liquid permeable sheet (top sheet) through which an aqueous liquid permeates and a liquid impermeable sheet (back sheet) through which an aqueous liquid does not permeate and is used, for example, as sanitary supplies for receiving a body fluid such as urine or blood, such as paper diapers and menstrual sanitary products; and so-called pet sheets for pet animals. In case of pet sheets, the aqueous liquid to be absorbed by the pet sheets is assumed to be fluid feeds, beverages and the like, in addition to body fluids of animals.

Examples of the liquid permeable sheet which can be used herein include nonwoven fabrics made of polyethylene, polypropylene, polyester and polyamide, and porous synthetic resin sheets. Examples of the liquid impermeable sheet include a film made of a synthetic resin and a sheet made of a composite material composed of a film made of a synthetic resin and a nonwoven fabric. The synthetic resin may be polyethylene, polypropylene, polyester, polyamide or the like.

The size and shape of the absorbent article can be arbitrarily set according to the intended use, and the absorbent article is used so that the side of a liquid permeable sheet can be the surface in contact with the body, or the surface on which animals lie down.

EXAMPLES

The present invention will be specifically described below by way of examples and comparative examples, but the present invention is not limited to these examples.

Example 1

Preparation of First Aqueous Solution

In a 500 ml Erlenmeyer flask, 92 g of an aqueous solution containing 80.5% by mass acrylic acid was charged, neutralized to 94 mol % by adding dropwise 165.3 g of an aqueous solution containing 23.4% by mass sodium hydroxide while externally cooling the flask, and then completely dissolved by stirring at room temperature. To the resulting solution, 0.11 g of potassium persulfate and 9.2 mg of N,N'-methylenebisacrylamide were added and dissolved to prepare a first aqueous solution of a monomer.

Preparation of Second Aqueous Solution

In a 500 ml Erlenmeyer flask, 110.4 g of an aqueous solution containing 80.5% by mass acrylic acid was charged, and then neutralized to 56 mol % by adding dropwise 115.7 g of an aqueous solution containing 23.9% by mass sodium hydroxide while externally cooling the flask. To the resulting solution, 0.13 g of potassium persulfate and 11.0 mg of N,N'-methylenebisacrylamide were added and dissolved to prepare a second aqueous solution of a monomer. This second aqueous solution was maintained at a temperature of about 23° C.

Step 1

A cylindrical round bottom separable flask having an inner diameter of 100 mm equipped with a reflux condenser, a dropping funnel, a nitrogen gas introducing tube and a stirrer (stirring blade including two-tiered 4-pitched-blade paddle impellers each having a blade diameter of 50 mm) was prepared. In this flask, 500 ml of n-heptane was charged and then 0.92 g of a sucrose stearate having the HLB of 3 (manufactured by Mitsubishi-Kagaku Foods Corporation under the trade name of "Ryoto Sugar Ester S-370") and 0.92 g of a maleic anhydride-modified ethylene-propylene copolymer (manufactured by Mitsui Chemicals, Inc. under the trade name of "Hi-WAX 1105A") were added. After being dissolved by heating to 80° C., the mixture was cooled to 50° C.

After setting the rotational speed of the stirrer to 450 rpm, the first aqueous solution was added in the separable flask and maintained at 35° C. for 30 minutes while replacing the atmosphere inside the flask with nitrogen. Then, the flask was heated by immersion in a water bath of 70° C. thereby performing polymerization to obtain a slurry of spherical primary particles. Using an oil bath of 120° C., azeotropic distillation of water and n-heptane was performed thereby removing water only off the system from a part of the slurry, and then n-heptane was vaporized, followed by drying to obtain spherical primary particles having a median particle size of 80 μm. This median particle size was measured by the method described in the below-mentioned evaluation (provided that "water-absorbent resin" is read as "primary particles") using a slurry obtained by performing step 1, apart from the slurry to be applied to the below-mentioned step 2. Such a method of measuring a median particle size of primary particles was employed because of satisfactory reproducibility of step 1, and the same method applied to the below-mentioned other examples and comparative examples.

Step 2

After changing the rotational speed of stirring of the slurry obtained in step 1 to 1,000 rpm and cooling to 23° C., the second aqueous solution was added to the slurry. After maintaining the flask for 30 minutes while replacing the atmosphere inside the flask with nitrogen, the flask was heated by immersion again in a water bath of 70° C. thereby performing polymerization to obtain a slurry containing secondary particles in which primary particles are agglomerated.

Post-Crosslinking Step

After step 2, the flask was heated using an oil bath of 120° C. and azeotropic distillation of water and n-heptane was performed thereby removing 236.8 g of water off the system while refluxing n-heptane. To the contents in the flask, 8.10 g of an aqueous solution containing 2% ethylene glycol diglycidyl ether as a post-crosslinking agent was added. After the flask was maintained at 80° C. for 2 hours, n-heptane was vaporized, followed by drying to obtain 213.7 g of a water-absorbent resin composed of secondary particles having a crosslinked surface.

Example 2

In a 500 ml Erlenmeyer flask, 92 g of an aqueous solution containing 80.5% by mass acrylic acid was charged and neutralized to 90 mol % by adding dropwise 156.2 g of an aqueous solution containing 23.7% by mass sodium hydroxide while externally cooling the flask, and then completely dissolved by stirring at room temperature. To the resulting solution, 0.11 g of potassium persulfate and 9.2 mg of N,N'-methylenebisacrylamide were added and dissolved to prepare a first aqueous solution of a monomer.

In a separate 500 ml Erlenmeyer flask, 119.6 g of an aqueous solution containing 80.5% by mass acrylic acid was charged, and then neutralized to 60 mol % by adding dropwise 139.5 g of an aqueous solution containing 23.0% by mass sodium hydroxide while externally cooling the flask. To the resulting solution, 0.14 g of potassium persulfate and 12.0 mg of N,N'-methylenebisacrylamide were added and dissolved to prepare a second aqueous solution of a monomer. This second aqueous solution was maintained at a temperature of about 23° C.

Using the above-mentioned first aqueous solution and second aqueous solution, steps 1 and 2 of Example 1 were performed in the same manner to obtain a slurry containing secondary particles in which primary particles (median particle size of 80 μm) are agglomerated. With respect to this slurry, the post-crosslinking step of Example 1 was carried out. In the post-crosslinking step, the amount of water removed off the system by azeotropic distillation of water and n-heptane was changed to 251.3 g, and the addition amount of the aqueous solution containing 2% ethylene glycol diglycidyl ether was changed to 8.46 g, respectively to obtain 222.0 g of a water-absorbent resin composed of secondary particles having a crosslinked surface.

Example 3

Preparation of First Aqueous Solution

In a 500 ml Erlenmeyer flask, 92 g of an aqueous solution containing 80.5% by mass acrylic acid was charged, neutralized to 85 mol % by adding dropwise 141.0 g of an aqueous solution containing 24.8% by mass sodium hydroxide while externally cooling the flask, and then completely dissolved by stirring at room temperature. To the resulting solution, 0.11 g of potassium persulfate and 9.2 mg of N,N'-methylenebisacrylamide were added and dissolved to prepare a first aqueous solution of a monomer.

Preparation of Second Aqueous Solution

In a separate 500 ml Erlenmeyer flask, 128.8 g of an aqueous solution containing 80.5% by mass acrylic acid was charged, and then neutralized to 65 mol % by adding dropwise 167.1 g of an aqueous solution containing 22.4% by mass sodium hydroxide while externally cooling the flask. To the resulting solution, 0.15 g of potassium persulfate and 12.9 mg of N,N'-methylenebisacrylamide were added and dissolved to prepare a second aqueous solution of a monomer. This second aqueous solution was maintained at a temperature of about 22° C.

Step 1

A cylindrical round bottom separable flask having an inner diameter of 100 mm equipped with a reflux condenser, a dropping funnel, a nitrogen gas introducing tube and a stirrer (stirring blade including two-tiered 4-pitched-blade paddle impellers each having a blade diameter of 50 mm) was prepared. In this flask, 500 ml of n-heptane was charged and then 0.92 g of a sucrose stearate having the HLB of 3 (manufactured by Mitsubishi-Kagaku Foods Corporation under the trade name of "Ryoto Sugar Ester S-370") and 0.92 g of a maleic anhydride-modified ethylene-propylene copolymer (manufactured by Mitsui Chemicals, Inc. under the trade name of "Hi-WAX 1105A") were added. After being dissolved by heating to 80° C., the mixture was cooled to 50° C.

After setting the rotational speed of the stirrer to 500 rpm, the first aqueous solution was added in the separable flask and maintained at 35° C. for 30 minutes while replacing the atmosphere inside the flask with nitrogen. Then, the flask was heated by immersion in a water bath of 70° C. thereby performing polymerization to obtain a slurry of spherical primary particles. Using an oil bath of 120° C., azeotropic distillation of water and n-heptane was performed thereby removing water only off the system from a part of the slurry, and then n-heptane was vaporized, followed by drying to obtain spherical primary particles having a median particle size of 60 μm.

Step 2

After changing the rotational speed of stirring of the slurry obtained in step 1 to 1,000 rpm and cooling to 22° C., the second aqueous solution was added to the slurry. After maintaining the flask for 30 minutes while replacing the atmosphere inside the flask with nitrogen, the flask was heated by immersion again in a water bath of 70° C. thereby performing polymerization to obtain a slurry containing secondary particles in which primary particles are agglomerated.

Post-Crosslinking Step

After step 2, the flask was heated using an oil bath of 120° C. and azeotropic distillation of water and n-heptane was performed thereby removing 257.3 g of water off the system while refluxing n-heptane. To the contents in the flask, 8.83 g of an aqueous solution containing 2% ethylene glycol diglycidyl ether as a post-crosslinking agent was added. After the flask was maintained at 80° C. for 2 hours, n-heptane was vaporized, followed by drying to obtain 231.1 g of a water-absorbent resin composed of secondary particles having a crosslinked surface.

Example 4

Preparation of First Aqueous Solution

In a 500 ml Erlenmeyer flask, 92 g of an aqueous solution containing 80.5% by mass acrylic acid was charged, neutralized to 90 mol % by adding dropwise 156.2 g of an aqueous solution containing 23.7% by mass sodium hydroxide while externally cooling the flask, and then completely dissolved by stirring at room temperature. To the resulting solution, 0.11 g of potassium persulfate and 9.2 mg of ethylene glycol diglycidyl ether were added and dissolved to prepare a first aqueous solution of a monomer.

Preparation of Second Aqueous Solution

In a separate 500 ml Erlenmeyer flask, 128.8 g of an aqueous solution containing 80.5% by mass acrylic acid was charged, and then neutralized to 60 mol % by adding dropwise 150.2 g of an aqueous solution containing 23.0% by mass sodium hydroxide while externally cooling the flask. To the resulting solution, 0.15 g of potassium persulfate and 12.9 mg of N,N'-methylenebisacrylamide were added and dissolved to prepare a second aqueous solution of a monomer. This second aqueous solution was maintained at a temperature of about 23° C.

Step 1

A cylindrical round bottom separable flask having an inner diameter of 100 mm equipped with a reflux condenser, a dropping funnel, a nitrogen gas introducing tube and a stirrer (stirring blade including two-tiered 4-pitched-blade paddle impellers each having a blade diameter of 50 mm) was prepared. In this flask, 500 ml of n-heptane was charged and then 0.92 g of a maleic anhydride-modified ethylene-propylene copolymer (manufactured by Mitsui Chemicals, Inc. under the trade name of "Hi-WAX 1105A") was added. After being dissolved by heating to 80° C., the mixture was cooled to 60° C.

After setting the rotational speed of the stirrer to 300 rpm, the first aqueous solution was added in a lump to the separable flask using the funnel. After setting the inner temperature to 40° C., the first aqueous solution was dispersed by stirring for 10 minutes. Subsequently, a solution prepared by dissolving 0.92 g of a sucrose stearate having the HLB of 3 (manufactured by Mitsubishi-Kagaku Foods Corporation under the trade name of "Ryoto Sugar Ester S-370") as a surfactant in 8.5 g of n-heptane with heating was added to the separable flask using the funnel. After changing the stirring rate to 500 rpm, the first aqueous solution was further dispersed.

After setting the rotational speed of the stirrer to 450 rpm, the separable flask was maintained at 40° C. for 30 minutes while replacing the atmosphere inside the separable flask with nitrogen. Then, the flask was heated by immersion in a water bath of 70° C. thereby performing polymerization to obtain a slurry of spherical primary particles. Using an oil bath of 120° C., azeotropic distillation of water and n-heptane was performed thereby removing water only off the system from a part of the slurry, and then n-heptane was vaporized, followed by drying to obtain spherical primary particles having a median particle size of 80 μm.

Step 2

After changing the rotational speed of stirring of the slurry obtained in step 1 to 1,000 rpm and cooling to 23° C., the second aqueous solution was added to the slurry. After maintaining the flask for 30 minutes while replacing the atmosphere inside the flask with nitrogen, the flask was heated by immersion again in a water bath of 70° C. thereby performing polymerization to obtain a slurry containing secondary particles in which primary particles are agglomerated.

Post-Crosslinking Step

After step 2, the flask was heated using an oil bath of 120° C. and azeotropic distillation of water and n-heptane was performed thereby removing 251.7 g of water off the system while refluxing n-heptane. To the contents in the flask, 8.83 g of an aqueous solution containing 2% ethylene glycol diglycidyl ether as a post-crosslinking agent was added. After the flask was maintained at 80° C. for 2 hours, n-heptane was vaporized, followed by drying to obtain 230.9 g of a water-absorbent resin composed of secondary particles having a crosslinked surface.

Comparative Example 1

Preparation of First Aqueous Solution

In a 500 ml Erlenmeyer flask, 92 g of an aqueous solution containing 80.5% by mass acrylic acid was charged, neutralized to 64 mol % by adding dropwise 118.6 g of an aqueous solution containing 22.2% by mass sodium hydroxide while externally cooling the flask, and then completely dissolved by stirring at room temperature. To the resulting solution, 0.11 g of potassium persulfate and 9.2 mg of N,N'-methylenebisacrylamide were added and dissolved to prepare a first aqueous solution of a monomer.

Preparation of Second Aqueous Solution

In a 500 ml Erlenmeyer flask, 101.2 of an aqueous solution containing 80.5% by mass acrylic acid was charged, and then neutralized to 64 mol % by adding dropwise 130.5 g of an aqueous solution containing 22.2% by mass sodium hydroxide while externally cooling the flask. To the resulting solution, 0.12 g of potassium persulfate and 10.1 mg of N,N'-methylenebisacrylamide were added and dissolved to prepare a second aqueous solution of a monomer. This second aqueous solution was maintained at a temperature of about 23° C.

Step 1

A cylindrical round bottom separable flask having an inner diameter of 100 mm equipped with a reflux condenser, a dropping funnel, a nitrogen gas introducing tube and a stirrer (stirring blade including two-tiered 4-pitched-blade paddle impellers each having a blade diameter of 50 mm) was prepared. In this flask, 500 ml of n-heptane was charged and then 0.92 g of a sucrose stearate having the HLB of 3 (manufactured by Mitsubishi-Kagaku Foods Corporation under the trade name of "Ryoto Sugar Ester S-370") and 0.92 g of a maleic anhydride-modified ethylene-propylene copolymer (manufactured by Mitsui Chemicals, Inc. under the trade name of "Hi-WAX 1105A") was added. After being dissolved by heating to 80° C., the mixture was cooled to 50° C.

After setting the rotational speed of the stirrer to 450 rpm, the first aqueous solution was added to the separable flask and maintained at 35° C. for 30 minutes while replacing the atmosphere inside the separable flask with nitrogen. Then, the flask was heated by immersion in a water bath of 70° C. thereby performing polymerization to obtain a slurry of spherical primary particles. Using an oil bath of 120° C., azeotropic distillation of water and n-heptane was performed thereby removing water only off the system from a part of the slurry, and then n-heptane was vaporized, followed by drying to obtain spherical primary particles having a median particle size of 80 μm.

Step 2

After changing the rotational speed of stirring of the slurry obtained in step 1 to 1,000 rpm and cooling to 23° C., the second aqueous solution was added to the slurry. After maintaining the flask for 30 minutes while replacing the atmosphere inside the flask with nitrogen, the flask was heated by immersion again in a water bath of 70° C. thereby performing polymerization to obtain a slurry containing secondary particles in which primary particles are agglomerated.

Post-Crosslinking Step

After step 2, the flask was heated using an oil bath of 120° C. and azeotropic distillation of water and n-heptane was performed thereby removing 212.3 g of water off the system while refluxing n-heptane. To the contents in the flask, 7.73 g of an aqueous solution containing 2% ethylene glycol diglycidyl ether as a post-crosslinking agent was added. After the flask was maintained at 80° C. for 2 hours, n-heptane was vaporized, followed by drying to obtain 196.3 g of a water-absorbent resin composed of secondary particles having a crosslinked surface.

Comparative Example 2

In a 500 ml Erlenmeyer flask, 92 g of an aqueous solution containing 80.5% by mass acrylic acid was charged and neutralized to 68 mol % by adding dropwise 131.4 g of an aqueous solution containing 21.3% by mass sodium hydroxide while externally cooling the flask, and then completely dissolved by stirring at room temperature. To the resulting solution, 0.11 g of potassium persulfate and 9.2 mg of N,N'-methylenebisacrylamide were added and dissolved to prepare a first aqueous solution of a monomer.

Using the above-mentioned first aqueous solution and the second aqueous solution prepared in the same manner as the second aqueous solution used in Example 3, steps 1 and 2 of Example 3 were performed in the same manner to obtain a slurry containing secondary particles in which primary particles (median particle size of 60 μm) are agglomerated. With respect to this slurry, the post-crosslinking step of Example 3 was carried out. In the post-crosslinking step, the amount of water removed off the system by azeotropic distillation of water and n-heptane was changed to 256.9 g to obtain 229.8 g of a water-absorbent resin composed of secondary particles having a crosslinked surface.

Comparative Example 3

In a 500 ml Erlenmeyer flask, 92 g of an aqueous solution containing 80.5% by mass acrylic acid was charged, neutralized to 95 mol % by adding dropwise 146.9 g of an aqueous solution containing 26.6% by mass sodium hydroxide while externally cooling the flask, and then completely dissolved by stirring at room temperature. To the resulting solution, 0.11 g of potassium persulfate and 9.2 mg of N,N'-methylenebisacrylamide were added and dissolved to prepare a first aqueous solution of a monomer.

In a separate 500 ml Erlenmeyer flask, 101.2 g of an aqueous solution containing 80.5% by mass acrylic acid was charged, and then neutralized to 95 mol % by adding dropwise 161.6 g of an aqueous solution containing 26.6% by mass sodium hydroxide while externally cooling the flask. To the resulting solution, 0.12 g of potassium persulfate and 10.1 mg of N,N'-methylenebisacrylamide were added and dissolved to prepare a second aqueous solution of a monomer. This second aqueous solution was maintained at a temperature of about 23° C.

Using the above-mentioned first aqueous solution and second aqueous solution, steps 1 and 2 of Comparative Example 1 were performed in the same manner to obtain a slurry containing secondary particles in which primary particles (median particle size of 80 μm) are agglomerated. With respect to this slurry, the post-crosslinking step of Comparative Example 1 was carried out. In the post-crosslinking step, the amount of water removed off the system by azeotropic distillation of water and n-heptane was changed to 254.0 g, and the addition amount of the aqueous solution containing 2% ethylene glycol diglycidyl ether was changed to 7.73 g, respectively to obtain 212.2 g of a water-absorbent resin composed of secondary particles having a crosslinked surface.

Comparative Example 4

The first aqueous solution similar to that used in Comparative Example 1 was prepared. In a separate 500 ml Erlenmeyer flask, 128.8 g of an aqueous solution containing 80.5% by mass acrylic acid was charged, and then neutralized to 95 mol % by adding dropwise 205.7 of an aqueous solution containing 26.6% by mass sodium hydroxide while externally cooling the flask. To the resulting solution, 0.15 g of potassium persulfate and 12.9 mg of N,N'-methylenebisacrylamide were added and dissolved to prepare a second aqueous solution of a monomer. This second aqueous solution was maintained at a temperature of about 23° C.

Using the above-mentioned first aqueous solution and second aqueous solution, steps 1 and 2 of Comparative Example 1 were performed in the same manner to obtain a slurry containing secondary particles in which primary particles (median particle size of 80 μm) are agglomerated. With respect to this slurry, the post-crosslinking step of Comparative Example 1 was carried out. In the post-crosslinking step, the amount of water removed off the system by azeotropic distillation of water and n-heptane was changed to 269.7 g, and the addition amount of the aqueous solution containing 2% ethylene glycol diglycidyl ether was changed to 8.83 g, respectively to obtain 232.5 g of a water-absorbent resin composed of secondary particles having a crosslinked surface.

Evaluation

With respect to water-absorbent resins obtained in the respective examples and comparative examples, the median particle size, uniformity of particle size distribution, moisture content, absorption capacity of saline solution, water-absorption capacity under load, remaining amount of dispersion medium (amount of petroleum-type hydrocarbon dispersion medium remaining inside water-absorbent resin particle) and pH of gel were measured, and also initial odor and odor with the lapse of time were evaluated. The measuring methods and evaluation methods are as follows. The results are shown in Table 2.

(1) Median Particle Size

The following two kinds of combined sieves were prepared.

(A) Japan Industrial Standard (JIS) standard sieves were stacked downward as follows; beginning with a sieve with a sieve opening of 425 μm at the top, followed by a sieve with a sieve opening of 250 μm, a sieve with a sieve opening of 180 μm, a sieve with a sieve opening of 150 μm, a sieve with a sieve opening of 106 μm, a sieve with a sieve opening of 75 μm, a sieve with a sieve opening of 45 μm and a tray in this order.

(B) Japan Industrial Standard (JIS) standard sieves were stacked downward as follows; beginning with a sieve with a sieve opening of 850 μm at the top, followed by a sieve with a sieve opening of 600 μm, a sieve with a sieve opening of 500 μm, a sieve with a sieve opening of 425 μm, a sieve with a sieve opening of 300 m, a sieve with a sieve opening of 250 μm, a sieve with a sieve opening of 150 μm and a tray in this order.

50 g of the water-absorbent resin was sieved with a JIS standard sieve with a sieve opening of 250 μm. The median particle size was measured by the following procedure, using the combined sieves (A) when 50% by mass or more of the resin passed through the sieve opening, while using the combined sieves (B) when 50% by mass or more of the resin remained on the sieve.

About 50 g of the water-absorbent resin was placed on the combined sieves at the top, and classified for 20 minutes using a ro-tap shaker. After the classification, the mass of the water-absorbent resin remaining on the respective sieves was calculated in terms of mass percentage relative to the total mass of the resin and the calculated values were integrated in order from the resins with a larger particle size, whereby, the relations between the sieve openings and the integrated values of the mass percentage of the water-absorbent resin remaining on the corresponding sieve were plotted on a logarithmic-probability paper. The plots on the paper were connected with a straight line, and the particle size corresponding to 50% by mass of the integrated mass percentage was defined as the median particle size.

(2) Uniformity of Particle Size Distribution

In the measurement of the median particle size, a particle size (X1) corresponding to 15.9% by mass of the integrated mass percentage and a particle size (X2) corresponding to 84.1% by mass of the integrated mass percentage were determined, and then uniformity of particle size distribution was determined by the following equation. This uniformity approaches 1 in case of narrow particle size distribution, while the uniformity becomes more than 1 when particle size distribution is widen.

$$\text{Uniformity} = X1/X2$$

(3) Moisture Content

About 2.5 g of the water-absorbent resin was weighed precisely in an aluminum cup (measuring mass: Wd) and, after drying at 105° C. using a hot air dryer for 2 hours, the mass (We) of the dried water-absorbent resin was measured again, and then the moisture content was calculated by the following equation. The tare mass of the aluminum cup before and after drying was assumed to be constant.

$$\text{Moisture content}(\%) = (Wd - We)/Wd \times 100$$

(4) Absorption Capacity of Saline Solution 500 g of an aqueous solution containing 0.9% by mass sodium chloride (saline solution) was charged in a 500 mL beaker with a rotator of 3 cm in length, and then 2.0 g (Wa) of the water-absorbent resin was weighed precisely and added to the beaker while stirring with a magnetic stirrer such that no unswollen lump is left. After stirring at a stirring speed of 600 rpm for 1 hour, the resulting aqueous solution containing the thus formed gel was filtered by a JIS standard sieve which is 20 cm in diameter with a sieve opening of 106 μm. Excessive water contained in the gel remaining on the sieve was roughly drained using a fluorine resin board, and then the sieve was tilted and left for 30 minutes for further draining. The weight (Wb) of the gel remaining on the sieve was weighed and then the absorption capacity of saline solution was calculated by the following equation.

$$\text{Absorption capacity of saline solution (g/g)} = Wb/Wa$$

(5) Absorption Capacity Under Load

Using a measuring apparatus 100 schematically shown in FIG. 1, the measurement was made. In the drawing, the measuring apparatus 100 includes a burette section 1, a conduit 2, a measurement stage 3, and a measurement section 4 placed on the measurement stage 3. The burette section 1 includes a burette 10. In this burette 10, the upper portion is closable by a rubber stopper 14, and an air introducing tube 11 and a cock 12 are connected to the lower portion. The air introducing tube 11 has a cock 13 at the tip. The conduit 2 has an inner diameter of 6 mm, and connects the cock 12 of the burette section 1 with the measurement stage 3. The height of the measurement stage 3 is vertically adjustable. The measurement stage 3 is provided with a hole (conduit port) having a diameter of 2 mm at the center, to which one end of the conduit 2 is connected. The measurement section 4 includes a cylinder 40 made of plexiglass, a polyamide mesh 41 bonded to the bottom of the cylinder 40, and a weight 42 which is vertically movable in the cylinder 40. The cylinder 40 can be disposed on the measurement stage 3 and the inner diameter thereof is 20 mm. The sieve opening size of the polyamide mesh 41 is 75 μm (200 mesh). The weight 42 has a diameter of 19 mm and a mass of 119.6 g. As described below, the weight 42 is used for applying a load of 4.14 kPa to a water-absorbent resin 5 spread uniformly over the polyamide mesh 41.

The water-absorption capacity under a load by this measuring apparatus 100 was measured in a room at 25° C. Specific procedure is as follows. First, the cocks 12 and 13 of the burette section 1 were closed and 0.9% by mass salt solution (saline solution) adjusted to 25° C. was charged from the upper portion of the burette 10. Next, the upper portion of the burette 10 was closed by the rubber stopper 14, and the cocks 12 and 13 were opened. Then, the height of the measurement stage 3 was adjusted so that the water level of saline solution coming out from the conduit port of the measurement stage 3 through the conduit 2 is even with the upper surface of the measurement stage 3. In the measurement section 4, 0.10 g of the water-absorbent resin 5 was uniformly spread over the polyamide mesh 41 in the cylinder 40, and the weight 42 was placed on the water-absorbent resin 5. Then, the cylinder 40 was disposed on the measurement stage 3 so that an axis line thereof agrees with the conduit port of the measurement stage 3.

A decrease in the amount of saline solution (i.e., amount of saline solution absorbed in the water-absorbent resin 5) Wc (ml) in the burette 10 was read 60 minutes after the beginning of absorption of saline solution from the conduit 2 by the water-absorbent resin 5. The water-absorption capacity of the water-absorbent resin 5 under a load was calculated by the following equation.

$$\text{Water-absorption capacity under load (ml/g)} = Wc \text{ (ml)}/0.10 \text{ (g)}$$

(6) Remaining Amount of Dispersion Medium

The amount of a petroleum-type hydrocarbon dispersion medium remaining in the water-absorbent resin was measured by the following procedure using a head space gas chromatograph.

(a) Preparation of Calibration Curve

After precisely weighing 0.1 g of a petroleum-type hydrocarbon dispersion medium (hereinafter sometimes referred to as a "dispersion medium") used in case of producing a water-absorbent resin to be measured in a 50 ml screw vial, DMF (dimethylformamide) was added therein to make the total amount 40 g. After precisely weighing the total amount, the content was stirred by a stirrer chip to give a standard sample solution. After precisely weighing 0.01 g, 0.04 g, 0.2 g and 0.5 g of the standard sample solution in four 20 ml-volume vial bottles (No. 5, manufactured by Maruemu Corporation) respectively, and DMF was added thereto to make the inner content of each vial bottle 0.75 g. Furthermore, 0.75 g of distilled water was added to each vial bottle and each bottle was closed by a septum gum and an aluminum cap, followed by fastening.

Each vial bottle was heated at 110° C. for 2 hours, and 1 ml of the vapor phase therein was collected and injected into a gas chromatograph to obtain a chromatogram. Based on a charge amount of a dispersion medium (i.e., a charge amount of a standard sample solution) in each vial bottle and a peak area of the chromatogram, a calibration curve was formed. When a mixture of a petroleum-type hydrocarbon dispersion medium is used as the dispersion medium, plural peaks appear on the chromatogram. Therefore, a calibration curve was formed based on a sum total area of the peaks and a charge amount.

(b) Measurement of Remaining Amount of Dispersion Medium in Water-Absorbent Resin About 2 g of a water-absorbent resin to be measured was charged in an aluminum cup and dried by a hot air dryer at 105° C. for 2 hours, thereby the moisture content of the resin was adjusted. After precisely weighing 0.10 g of the water-absorbent resin having the adjusted moisture content in a 20 ml-volume vial bottle (No. 5, manufactured by Maruemu Corporation), 0.75 g of DMF was added thereto and also 0.75 g of distilled water was added thereto. After slightly stirring by shaking the bottle, the bottle was closed with a septum gum and an aluminum cap, followed by fastening. Herein, the water-absorbent resin was swollen slowly and uniformly by adding the distilled water in the presence of DMF, thereby the dispersion medium included in the water-absorbent resin was extracted. Then, the vial bottle was heated at 110° C. for 2 hours, and 1 ml of the vapor phase therein was collected and injected into a gas chromatograph to obtain a chromatogram.

The amount of the dispersion medium contained in 0.10 g of the water-absorbent resin was calculated by the prepared calibration curve based on a peak area of the obtained chromatogram, and then the obtained numerical value was converted into the amount (ppm) of the dispersion medium contained per 1 g of the sample.

In this measurement, the conditions of a gas chromatograph were set as follows.
Model: GC-14A+HSS2B (Headspace Autosampler) manufactured by Shimadzu Corporation
Filler: Squalane 25% Shimalite (NAW) (101) 80 to 100 mesh
Column: 3.2 mmφ×2 m
Column temperature: 80° C.
Injection port temperature: 180° C.
Detector temperature: 180° C.
Detector: FID
Gas carrier: nitrogen
Vial bottle heating temperature: 110° C.
Syringe temperature: 110° C.

(7) pH of Gel

After weighing 49.0 g of saline solution in a 100 mL-volume beaker, a magnetic stirrer bar (8 mmφ×30 mm in size with no ring) was put in the beaker and the beaker was placed on a magnetic stirrer. After adjusting so that the magnetic stirrer bar rotates at 600 rpm, 1.0 g of a water-absorbent resin was added and stirring was continued until vortex by circulation disappeared and the liquid level became horizontal to prepare a swollen gel as a measuring sample.

A pH meter (manufactured by HORIBA, Ltd. under the trade name of "F-24II") equipped with a flat type pH composite electrode (manufactured by HORIBA, Ltd. under the trade name of "6261-10C") was calibrated with a standard solution at pH 4, 7 and 9 in advance. The tip of the pH composite electrode was slightly brought into contact with a surface of the swollen gel, which was left for 10 minutes after swelling, thereby the pH of the gel was measured.

(8) Initial Odor Test 25 g of urea, 9 g of sodium chloride, 0.6 g of magnesium sulfate (heptahydrate), 0.7 g of calcium lactate, 4 g of potassium sulfate and 2.5 g of ammonium sulfate were dissolved and mixed in 1 L of distilled water to prepare artificial urine. Also, urease (1,000 U/ml of a 50% glycerin solution originating from Sword Bean (*Canavalia gladiata*) manufactured by MERCK) was diluted with distilled water 1,000 times to prepare a urease liquid.

Odor of the water-absorbent resin originating from the dispersion medium upon swelling was compared by the following method. 20.0 g of the artificial urine of 35° C. and 0.6 g of the urease liquid were charged in a 140 mL glass bottle with a cap (mayonnaise bottle) and stirred by a rotor of 3 cm in length. 4.0 g of the water-absorbent resin was added to the glass bottle and the bottle was tightly sealed. After the lapse of 10 minutes, odor originating from the dispersion medium in the glass bottle was evaluated. Herein, odor was judged by five panelists in accordance with the "six-level odor intensity indication method" shown in Table 1 and the average was regarded as initial odor.

TABLE 1

| Evaluation | Evaluation criteria |
| --- | --- |
| 5 | Overpowering odor |
| 4 | Strong odor |
| 3 | Easily perceptible odor |
| 2 | Slight odor, odor of what is recognized |
| 1 | Barely perceptible odor |
| 0 | No odor |

(9) Test of Odor with Lapse of Time

The glass bottle sealed by the cap, which contains the water-absorbent resin subjected to the evaluation of initial odor, was stored in an incubator of 35° C. after the initial odor test (8). After the lapse of 8 hours, odor in the glass bottle was evaluated. Herein, similar to the initial odor test, odor was judged by five panelists in accordance with the "six-level odor intensity indication method" shown in Table 1 and the average was regarded as odor with the lapse of time.

TABLE 2

|  | First aqueous solution (A) | | Second aqueous solution (B) | | Molar neutralization degree Z (%) of water-absorbent resin | Median particle size (μm) | Uniformity of particle size distribution |
| --- | --- | --- | --- | --- | --- | --- | --- |
|  | Molar neutralization degree X (%) | Monomer concentration (% by mass) | Molar neutralization degree Y (%) | Monomer concentration (% by mass) | | | |
| Example 1 | 94 | 37 | 56 | 46 | 73 | 420 | 1.7 |
| Example 2 | 90 | 38 | 60 | 44 | 73 | 450 | 1.9 |
| Example 3 | 85 | 40 | 65 | 42 | 73 | 380 | 1.6 |
| Example 4 | 90 | 38 | 60 | 44 | 73 | 370 | 1.8 |
| Comparative Example 1 | 64 | 42 | 64 | 42 | 64 | 360 | 2.0 |
| Comparative Example 2 | 68 | 40 | 65 | 42 | 66 | 390 | 1.9 |
| Comparative Example 3 | 95 | 40 | 95 | 40 | 95 | 400 | 1.6 |
| Comparative Example 4 | 64 | 42 | 95 | 40 | 82 | 370 | 2.1 |

TABLE 2-continued

|  | Moisture content (%) | Water-absorption capacity of saline solution (g/g) | Water-absorption capacity under load (ml/g) | Remaining amount of dispersion medium (ppm) | pH of gel | Initial odor | Odor with lapse of time |
|---|---|---|---|---|---|---|---|
| Example 1 | 6 | 60 | 18 | 520 | 5.7 | 0.4 | 1.8 |
| Example 2 | 7 | 66 | 14 | 600 | 5.7 | 0.4 | 1.4 |
| Example 3 | 6 | 56 | 21 | 650 | 5.8 | 0.4 | 1.4 |
| Example 4 | 8 | 48 | 25 | 75 | 5.7 | 0.2 | 1.1 |
| Comparative Example 1 | 6 | 59 | 15 | 7,300 | 5.5 | 3.6 | 2.2 |
| Comparative Example 2 | 7 | 63 | 13 | 6,100 | 5.5 | 3.4 | 2.2 |
| Comparative Example 3 | 8 | 66 | 12 | 580 | 8.7 | 0.4 | 4.2 |
| Comparative Example 4 | 8 | 58 | 14 | 7,000 | 6.8 | 3.4 | 3.6 |

As is apparent from Table 2, in case of the water-absorbent resin obtained in Examples 1 to 4, initial odor originating from the dispersion medium is reduced because of small remaining amount of the dispersion medium used during production, and the generation of odor represented by ammonia with the lapse of time is also effectively suppressed.

The present invention can be carried out in other specific forms without departing from the spirit or essential properties thereof. The above embodiment and example are therefore to be considered in all respects as illustrative and not restrictive. The scope of the present invention is indicated by the appended claims rather than by the foregoing description. All changes and modifications which come within the range of equivalency of the claims are therefore intended to be included within the scope of the present invention.

The invention claimed is:

1. A method for producing a water-absorbent resin by a reversed-phase suspension polymerization method, the method comprising:
   step 1 of dispersing a first aqueous solution containing a partially neutralized product (A) of a water-soluble ethylenically unsaturated monomer having acid groups in the molecule in a petroleum-type hydrocarbon dispersion medium in the presence of a dispersing agent, and then polymerizing the resulting dispersion to obtain a slurry containing primary particles of a polymer, and
   step 2 of adding a second aqueous solution containing a partially neutralized product (B) of a water-soluble ethylenically unsaturated monomer having acid groups in the molecule to the slurry obtained in step 1, and then polymerizing the resulting mixture to obtain a slurry in which the primary particles are agglomerated, and
   a drying step of removing the petroleum-type hydrocarbon dispersion medium and moisture from the slurry obtained in step 2,
   wherein the dispersing agent is at least one member selected from the group consisting of a surfactant and a polymer-type dispersing agent, and
   a molar neutralization degree X of the partially neutralized product (A) is set larger than a molar neutralization degree Y of the partially neutralized product (B), and a difference between the molar neutralization degree X and the molar neutralization degree Y is set to 5% or more.

2. The method for producing a water-absorbent resin according to claim 1, wherein the addition and polymerization of the second aqueous solution are repeated in step 2.

3. The method for producing a water-absorbent resin according to claim 1, wherein the molar neutralization degree X is set to 65 to 94%, and the molar neutralization degree Y is set to 56 to 89%.

4. The method for producing a water-absorbent resin according to claim 1, wherein the water-soluble ethylenically unsaturated monomer having acid groups in the molecule is at least one member among those of acrylic acid and methacrylic acid.

5. The method for producing a water-absorbent resin according to claim 1, wherein the surfactant is at least one kind selected from the group consisting of a polyglyceryl fatty acid ester, a sucrose fatty acid ester and a sorbitan fatty acid ester.

6. The method for producing a water-absorbent resin according to claim 1, wherein the polymer-type dispersing agent is at least one kind selected from the group consisting of a maleic anhydride-modified polyethylene, a maleic anhydride-modified polypropylene, a maleic anhydride-modified ethylene-propylene copolymer, a maleic anhydride-ethylene copolymer, a maleic anhydride-propylene copolymer, a maleic anhydride-ethylene-propylene copolymer, a polyethylene, a polypropylene, an ethylene-propylene copolymer, an oxidized polyethylene, an oxidized polypropylene and an oxidized ethylene-propylene copolymer.

7. The method for producing a water-absorbent resin according to claim 1, wherein the first aqueous solution is dispersed in the petroleum-type hydrocarbon solvent containing the polymer-type dispersing agent, and the surfactant is further added to the obtained dispersion, and then the resulting mixture is polymerized in step 1.

8. The method for producing a water-absorbent resin according to claim 1, further comprising step 3 of post-crosslinking the water-absorbent resin obtained in step 2 using a post-crosslinking agent.

9. The method for producing a water-absorbent resin according to claim 8, wherein the post-crosslinking agent is at least one kind selected from the group consisting of ethylene glycol diglycidyl ether, polyethylene glycol diglycidyl ether, ethylene glycol triglycidyl ether, polyethylene glycol triglycidyl ether, glycerol diglycidyl ether, polyglycerol diglycidyl ether, glycerol triglycidyl ether, polyglycerol triglycidyl ether, propylene glycol polyglycidyl ether, polypropylene glycol polyglycidyl ether, glycerol polyglycidyl ether and polyglycerol polyglycidyl ether.

* * * * *